United States Patent [19]

Raban et al.

[11] Patent Number: 5,096,832
[45] Date of Patent: Mar. 17, 1992

[54] METHOD OF DETECTING CATIONS USING A TETRA SUBSTITUTED CYCLOHEXANE

[75] Inventors: Morton Raban, West Bloomfield; David T. Durocher, Garden City, both of Mich.

[73] Assignee: Wayne State University, Detroit, Mich.

[21] Appl. No.: 562,463

[22] Filed: Aug. 3, 1990

[51] Int. Cl.$^5$ ............................................. G01N 33/70
[52] U.S. Cl. ........................................ 436/74; 436/79; 436/166
[58] Field of Search ..................... 436/63, 73, 74, 79, 436/164, 174

[56] References Cited

U.S. PATENT DOCUMENTS 4,670,218 6/1987 Gantzer et al. ..................... 422/56
4,994,395 2/1991 Chapoteau et al. .................. 436/79

FOREIGN PATENT DOCUMENTS 0128196 1/1960 U.S.S.R. .

OTHER PUBLICATIONS

"Photoresponsive Crown Ethers. 1. Cis-Trnas Isomerism of Azobenzene as a Tool to Enforce Conformational Changes, etc.", Shinkai, S. et al., Am. Chem. Soc. 1980, 102, 5860–5865.
"1,2–Dithia–5,8,11,14–Tetraoxacyclohexadecane, etc", Raban, M. et al., Chem. Soc., Chem. Commun., 1983, 1409.
"Host–Guest Complexation, etc.", Cram; D. J., Brown; B. S., et al., Am. Chem. Soc., 1984, 106.
"'Flipped-Out' Ionophores Trans-Cyclohexano Pentaethylene Glycol Diethyl Ethers"; Raban, M., et al., Chem. Soc., Chem. Common, 1985, 1557.
"Preo–Organization–from Solvents to Spherands", Cram, D. J., Angew. Chem. Int. Ed. Engl., 1986, 25, 1039.
"Host–Guest Complexation. 44. Cavitands and Caviplexes, etc.", Burch, D. L., Master's Thesis, Wayne State University, 1987.
Hortelano, E. R. Doctorial Dissertation, Wayne State University, 1988 re: Switched-On Flipped-Out Ionophores.

Primary Examiner—David L. Lacey
Assistant Examiner—Thomas E. Daley
Attorney, Agent, or Firm—Brooks & Kushman

[57] ABSTRACT

Disclosed is a tetra substituted cyclohexane having an ionophore in the one and two positions wherein the ionophore may be the same or different and is selected from the group consisting of a crown, a podand and a cryptand wherein the ionophore is capable of complexing with a metal or ammonium cation. Positions four and five are substituted by an electron donor group and an electron acceptor group. Also disclosed is a method for detecting the concentration of cations in a fluid by subjecting the fluid to the tetra substituted cyclohexane composition which will thereby complex the cation in the fluid. The cations are preferably alkali metal and alkaline earth metal cations. The fluid may be an aqueous or non-aqueous fluid or body fluids.

16 Claims, 4 Drawing Sheets

METHOD OF DETECTING CATIONS USING A TETRA SUBSTITUTED CYCLOHEXANE

STATEMENT OF FEDERALLY SPONSORED RESEARCH

The funding for work described herein was provided in part by the Federal Government, under a grant from the National Institute of Health. The government may have certain rights in this invention.

TECHNICAL FIELD

The present invention is concerned with the field of conformationally biased intramolecular charge transfer complex containing ionophore cyclohexane compositions.

BACKGROUND OF THE INVENTION

Ionophores are materials capable of forming complexes with charged species, preferably cations. Chromophores are chemical groups which when present in a compound give color to the compound by causing a displacement of, or appearance of, absorbance bands in the visible spectrum.

The equilibrium constants for alkali metal complexation of polyethylene glycol ethers can be measured by low temperature nuclear magnetic resonance (NMR) spectroscopy by using a method which makes use of conformational biasing. "Flipped-out" ionophores, such as trans-cyclohexano pentaethylene glycol diethyl ethers for the complexation of metal ions are disclosed in the *Journal of The Chemical Society, Chemical Communications* 1983, page 1409, M. Raban et al. An oral presentation as to conformationally biased intramolecular charged transfer interaction was made in the Spring of 1989 at the Wayne State University, Department of Chemistry, Detroit, Mich. by D. Durocher et al which disclosed the ketal 4-methylthiophenoxy-8,8-dimethyl-[4.3.0]-bicyclo-7,9-dioxo-nonane-3-ol-3,5-dinitro benzoate.

The addition of barium and calcium to an azulene crown ether has been reported as resulting in a shift in the UV-visible absorbance spectra of the material. *Chem. Ber.*, 1984, 117, 2839, H. G. Lohr, F. Vogtle, H. Puff and W. Schuh. Since the donor atoms of the ionophore are not directly incorporated into the chromophore, the shift in spectra must be due to the interaction of the cation with the negatively polarized five-membered ring in the azulene moiety. This interaction serves to stabilize the ground state and destabilize the excited state.

Chromoionophores have been developed that upon complexation exhibit bathochromic shifts, in the absorption maximum of the UV-visible spectrum. For this to occur, the donor portion of the ionophore that is incorporated into the chromophore must be attached at its electron-poor end. Quinone imine ionophore shows a bathochromic shift upon the addition of metal cations. *Chem. Ber.* 1981, 114, 638 J. Dix and F. Vogtle. An amino azulene chromoionophore shows significant bathochromic shift upon the addition of barium with the solution turning yellow to blue-violet. *Chem. Ber.* 1985, 118, 256, H. G. Lohr and F. Vogtle. Another chromoionophore that exhibits a large bathochromic shift in the presence of pyridine/lithium is an azophenol crown reported in *Tetrahedron Lett.*, 1981, 22, 4407, T. Kaneda, K. Sugihara, H. Kamiya and S. Mitsumi. On addition of lithium chloride, the yellowish solution turns deep purple. Other alkali metal cations show no change in the spectra. The material azophenol cryptand shows a high selectivity for potassium in dioxane/morpholine as reported in European patent application 83100281. The color change allows the quantitative determination of potassium in solution or in test strips. In both cases, the material forms a neutral complex with the metal ion in the presence of base.

It has been reported that the synthesis and characterization of chromogenic spherand ionophores have high affinity for alkaline metal cations. Spherand chromophores exhibit a high affinity for both potassium and sodium in 80% dioxane / 20% water upon addition of 1,5-diazabicyclo[4.3.0]non-5-ene, *Journal of American Chemical Society*, 1988, 110, 571 D. J. Cram, R. A. Carmack and R. C. Helgeson. Cram has also reported the synthesis and characterization of mixed sphero cryptand and sphero-crown type chromogenic ionophores. *Journal of American Chemical Society*, 1989, 111, 6339 R. C. Helgeson, B. P. Chech, E. Schapotau, C. R. Gebauer, A. Kumar and D. J. Cram.

None of the prior art demonstrates materials that have the capability of acting as both a chromophore and an ionophore whereby the ionophore can preferentially interact with metal ions and where there is a color change in the solution of the material but where the ionophore and chromophore are spacially separated and electronically insulated and where the color change derives primarily from a conformational change attendant upon complexation.

SUMMARY OF THE INVENTION

Described are tetrasubstituted cyclohexanes having ionophoric group(s) in the 1,2 position and chromophores in the 4,5 position wherein the ionophore groups are the same or different and may be a crown, podand or cryptand and are capable of complexing a metal ion or ammonium;

and wherein one chromophore is an electron donor moiety and the other is an electron acceptor moiety.

The invention is also concerned with the method of detecting cations in a fluid such as liquid comprising the steps of:

providing a cation or ammonium ion containing fluid such as liquid; and complexing the ion from the fluid by treating the fluid with an effective complexing amount of the above-identified tetra substituted cyclohexane composition.

DESCRIPTION OF PREFERRED EMBODIMENTS

Figure 1:
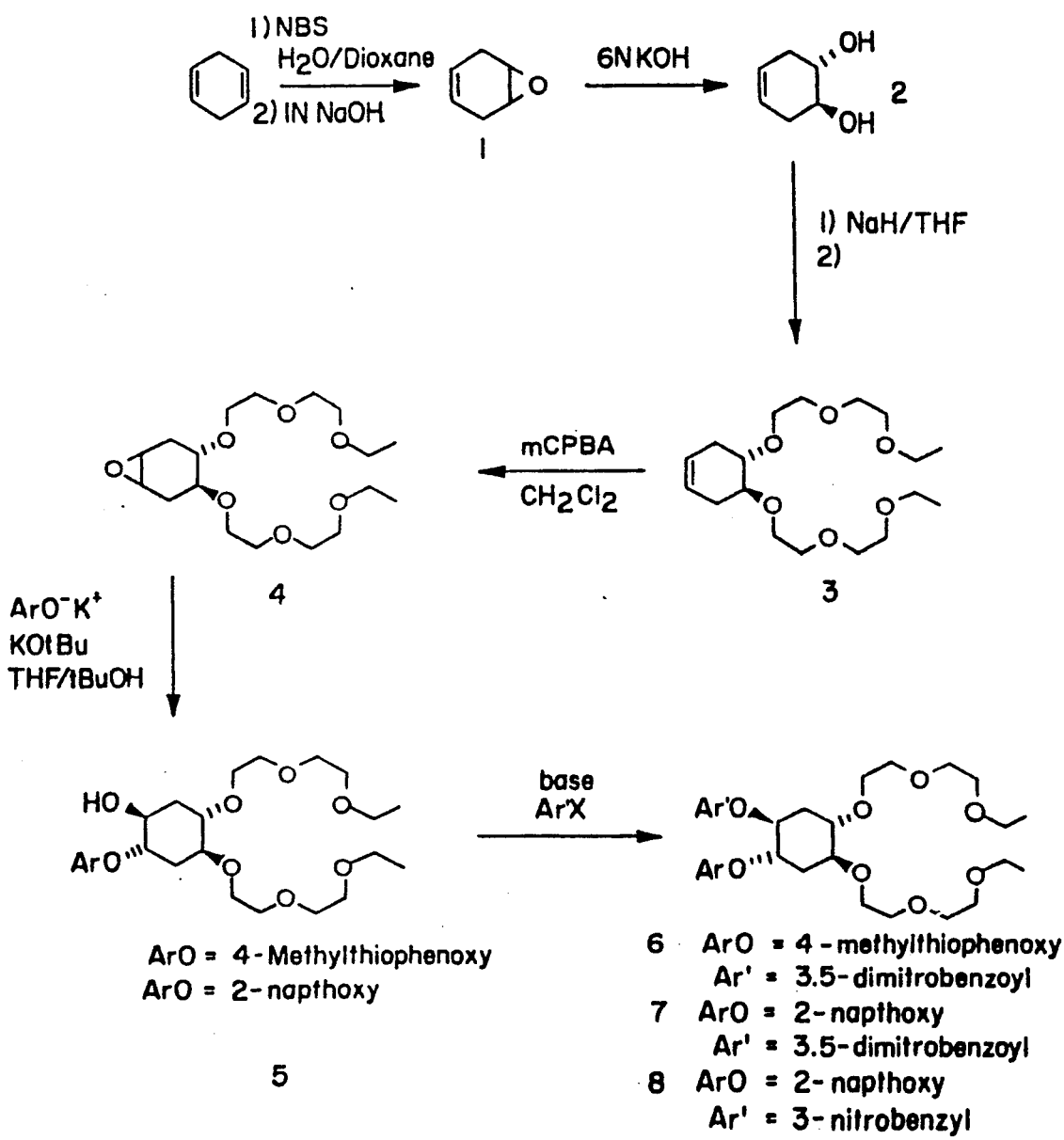
FIGS. 1 and 2 are schematic drawings of the techniques for preparing compounds of the present invention.

The tetra substituted cyclohexane compositions of the present invention are designed to have an intramolecular charge transfer chromogen and ionophore. Basically, the purpose of the composition is to complex the various metal ions such as alkali metal ions, alkaline earth metal ions and ammonium ions and to effect a change in the UV-visible spectrum upon complexation.

The alkali metal ions include lithium, sodium, potassium and the like. The alkaline earth metal ions include calcium, magnesium, strontrum, barium and the like.

Ammonium ions are the fluid soluble ammonium ions that result from dissolving primary and secondary amines. The amine containing materials are alkyl amines, aralkyl amines and the hydroxy and carboxy derivatives thereof of from 6–20 carbon atoms. Suitable amines are para-3-amino propyl benzyl amine; amino acids may be cystine, phenylalanine, tyrosine, halogenated tyrosines, thyronine, halogenated thyronines, proline, tryptophan and the like.

Synthetic ionophores are materials that are capable of forming complexes with charged species, primarily cations. The common features shared by all ionophores are 1) the presence of an array of heteroatoms containing electron pairs capable of forming donor-acceptor complexes with cations and 2) a flexible hydrocarbon backbone capable of solvating the complex in both polar and nonpolar solvents. The geometry of the hydrocarbon backbone contained in synthetic ionophores facilitates their classification into three categories: acyclic podands (i.e. polyethers), monocyclic coronands (i.e. crown ethers) and multicyclic cryptands. Examples of each class are: pentaethylene glycol diethyl ether, 18-crown-6, an elipsoidal [2.2.2] cryptand, kryptofix-S, tetrathia-12-crown-4, and a spherical cryptand.

This case is further concerned with charge transfer complexes or switchable intramolecular charge-transfer complexes (sometimes called electron donor-acceptor complexes, Mulliken, R. S., J. Am. Chem. Soc. 1952, 74, 811, herein incorporated by reference). These complexes give rise to absorption bands that are not present in the two parent compounds that form the complex. The intensity of these absorption bands (and the extent of intramolecular complexation) can be controlled by changing the relative molecular geometry of the complex framework, which is accomplished by chemical manipulation of the parent compounds.

The interaction of a molecule of high electron affinity with another molecule possessing low ionization potential may give rise to a molecular complex (or charge transfer complex) possessing properties not found in either component substance. These properties are: 1) new electronic absorption bands, 2) a loss in diamagnetic susceptibility, and 3) an increase in paramagnetic susceptibility (the presence of unpaired electrons).

The purpose of the compositions is to permit the detection of these ions in fluids such as aqueous or non-aqueous liquids, mammallian body liquids such as blood, urine and the like and other liquid fluids in which the metal ions are dissolved such as liquid hydrocarbons, liquid halogenated hydrocarbons from one to six carbon atoms, aliphatic alcohols or esters, aliphatic glycols or glycol ethers, heterocyclic solvents such as dioxane, furan, pyridine and mixtures thereof.

Having described the invention, listed below are preferred embodiments wherein all parts are parts by weight and all temperatures are in degrees Centigrade unless otherwise indicated.

EXAMPLE 1

Synthesis of 1(S,R), 2(S,R), 4(S,R), 5(S,R)-2-(4-methylthiophenoxy)-4,5-bis (1,4,7-trioxanonanyl)-cyclohexyl-3,5-dinitrobenzoate The product was a result of the stepwise reaction scheme illustrated in FIG. 1.

The reaction steps proceeded as follows.

A. 1,4-Cyclohexadiene (50.0 g, 0.626 mol) was added to a mixture of 225 ml of distilled water and 25 ml of p-dioxane. The mixture was stirred at 25° C. and N-bromo succinimide (108.9 g, 0.612 mol) was added slowly over a 1 hour period. The mixture was allowed to stir an additional 3 hours. The reaction mixture was then extracted 3 times with 100 ml portions of chloroform. The combined organic layers were then extracted 3 times with 50 ml portions of saturated aqueous sodium bicarbonate then dried over sodium sulfate and filtered. The solvent was removed in vacuo and the crude bromohydrin was immediately added to 1050 ml of a freshly prepared 1.0 N sodium hydroxide solution and allowed to stir for 1 hour at 25° C. The reaction mixture was extracted three times with 100 ml portions of chloroform and the combined organic layers were dried over sodium sulfate and filtered. The solvent was removed in vacuo giving the crude epoxide which was distilled at 5 mm Hg. The fraction collected at 38°–40° C. (58.5 g, 97%) was shown to be subreaction product 1: [4.1.0] Bicyclo-7-oxo-hept-3-ene.

B. To 126 ml of a 6N solution of potassium hydroxide was added 15 ml of p-dioxane and 123.4 g (243.6 mmol) of [4.1.0] Bicyclo-7-oxo-hept-3-ene. The stirred mixture was allowed to reflux for 24 hours and then cooled to room temperature. 150 ml of brine was added and the mixture was extracted 7 times with 50 ml aliquots of chloroform. The combined organic layers were dried over sodium sulfate and the solvent was removed in vacuo. The resulting oil solidified upon standing giving the crude diol. The diol was dissolved in hot ethyl acetate, decolorized with activated charcoal and recrystallized from hot 75% ethyl acetate/25% heptane to give subreaction product 2, [1(R,S),2(R,S)]4-cyclohexen-1,2-diol as white crystals, 15.9 g (57.4%).

C. A 3 neck flask was fitted with a magnetic stirrer, a condenser and an addition funnel. The flask was flame dried and constantly purged with dry nitrogen. To the flask, 300 ml of dry THF and sodium hydride (2.78 g, 1.1 equiv., 50% oil dispersion, washed twice with hexane) were added and allowed to stir. [1(R,S),2(R,S)]4-Cyclohexen-1,2-diol (3.0 g, 26.3 mmol) and 18-crown-6 (0.10 g, catalyst) were added to the solution and stirred for 4 hours. The flask was put in a brine-ice bath (−5° C.) and 2-(2-ethoxyethoxy)ethyl p-toluene sulfonate (17.42 g, 1.15 equiv.) was dissolved in 50 ml of dry THF and added dropwise over a 2 hour period. The solution was warmed to room temperature and the flask was fitted with a heating mantle. The solution was heated and allowed to reflux for 48 hours, then cooled. The mixture was filtered and the solvent removed in vacuo. The product was separated by flash column chromatography (300 g silica gel, 40% ethyl acetate/60% petroleum ether rising to 75% ethyl acetate/25% petroleum ether, TLC:R$_f$diol=0.31, R$_f$product =0.39, in 50/50 EthOAc/Pet Eth) giving subreaction product 3, 4(S,R),5(S,R)-4,5-bis(1,4,7-trioxononanyl)-cyclohex-1-ene as a clear-yellowish oil (3.7 g, 41%).

The 2-(2-ethoxyethoxy)ethyl p-toluene sulfonate was prepared as follows: Pyridine (75 ml) was added to a flask containing p-toluene sulfonyl chloride (16.0 g, 0.085 mol) and swirled until the solid dissolved. The mixture was cooled to 0° C. and 2-(2-ethoxyethoxy) ethanol (11.4 g, 0.085 mol) was added. The mixture was stirred for 3 hours and 10% sulfuric acid added until the pH of the solution was 5 or less. The solution was then extracted 3 times with ether and the combined organic layers were dried over sodium sulfate. The solvent was removed in vacuo leaving an oil that was shown to be pure 2-(2-ethoxyethoxy)ethyl p-toluene sulfonate (16.1 g, 55%, 0.047 mol).

D. A 250 ml flask was flame dried and fitted with a drying tube and a magnetic stirrer. The flask was then charged with 125 ml of methylene chloride, 4(S,R),5(S,R)-4,5-bis(1,4,7-trioxononanyl)-cyclohex-1-ene-(1.5 g, 4.33 mmol) and chilled in an ice bath. The solution was allowed to stir for 15 minutes, then meta-chloroperoxy-benzoic acid (80%, 1.51 g, 8.5 mmol) was added and the solution was stirred for 2 hours. The reaction mixture was then warmed slowly to room temperature and allowed to stir overnight. The solvent was removed in vacuo while maintaining the bath temperature below 30° C. and the remaining oil was dissolved in 100 ml of ether. The organic solution was extracted 3 times with 20% aqueous sodium bisulfite, 3 times with saturated sodium bicarbonate and once with brine. The organic layer was dried over sodium sulfate and the solvent removed in vacuo. The crude oil was purified using flash chromatography (150 g silica gel, 40% ethyl acetate/60% petroleum ether yielding 1.263 g (64%) 1(R,S),2 (S, R),4 (S,R),5(S,R)-4,5-bis (1,4,7-trioxononanyl)-cyclohex-1-ene oxide (subreaction product 4), as a clear, white oil.

E. A 100 ml flask was flame dried and purged with dry nitrogen. The flask was fitted with a condenser, magnetic stirrer and charged with 25 ml of tert-butyl alcohol. 4-methylthiophenol (4 equivalents) was dissolved in 25 ml of dry THF and added to the reaction flask. To the solution, potassium tert-butoxide (0.747 g, 4.0 equivalents) was added and the solution was allowed to stir for 20 minutes. 1(R,S),2(S,R),4(S,R),5(S,R)-4,5-bis (1,4,7-trioxononanyl)-cyclohex-1-ene oxide (0.655 g, 1.81 mmol) was added to the mixture, the flask was fitted with a heating mantle and the mixture was warmed and allowed to reflux for 4 days. The solvent was removed in vacuo and the residue was dissolved in diethyl ether. The organic solution was extracted 3 times with 10% sodium hydroxide, once with brine and dried over magnesium sulfate. The solvent was removed in vacuo leaving pure 2-(4-methylthiophenoxy)-4,5-bis(1,4,7-trioxanonanyl)-1cyclohexanol (subreaction product 5) as a clear oil (92–97%).

F. A 50 ml flask was flame dried and fitted with a magnetic stirrer and a drying tube. Dry benzene (25 ml), pyridine (0.554 g, 3 equivalents), 4-dimethylaminopyridine (DMAP, 0.10 g, catalyst) and 2-(4-methylthiophenoxy-4,5-bis (1,4,7-trioxanonanyl)-1-cyclohexanol (1.755 mmol) were added and allowed to stir for 5 minutes until all of the added DMAP had dissolved. To the solution, 3,5-dinitrobenzoyl chloride (1.22 g, 3.9 equivalents) was added and the mixture was stirred for 24 hours. The solution was filtered through Celite and the solvent was stripped in vacuo. The crude oil was purified by column chromatography with 50/50 ethyl acetate/pet ether escalating to 100% ethyl acetate after 1 column volume. Final product 6, 2-(4-methythiophenoxy)-4,5-bis (1,4,7-trioxanonanyl) cyclohexyl -3,5-dintrobenzoate, was isolated as an orange oil in moderate yields (32–54%).

EXAMPLE 2

Synthesis of 1(S,R), 2(S,R), 4(S,R), 5(S,R)-2-(2-napthoxy)-4,5-bis (1,4,7-trioxanonanyl)-cyclohexyl-3,5-dinitrobenzoate The reaction synthesis proceeded as in Example 1 until subreaction E. Four equivalents of 2-napthol were added in place of the 4-methylthiophenol. After subreaction E produced the corresponding alcohol (subproduct 5), 2-(2-napthoxy)-4,5-bis(1,4,7 trioxanonanyl)-1-cyclohexanol, subreaction F proceeded as in Example 1 and produced 2-(2-napthoxy)-4,5-bis(1,4,7-trioxanonanyl)-cyclohexyl-3,5-dintrobenzoate, final product 7, which was purified and isolated as an orange or yellow oil in moderate yield (32–54%).

EXAMPLE 3

Synthesis of 1(S,R), 2(S,R), 4(S,R), 5(S,R)-2-(2-napthoxy)-4,5-bis (1,4,7-trioxanonanyl)-cyclohexyl-3-nitrobenzyl ether The reaction proceeded as in Example 2 for the synthesis of 2-(2-napthoxy)-4,5-bis(1,4,7-trioxanonanyl)-1-cyclohexanol.

A 100 ml flask was then flame dried, purged with dry nitrogen and fitted with a magnetic stirrer, condenser and dropping funnel. Dry THF (25 ml) was added to the flask and subproduct 5, 2-(2-napthoxy)-4,5bis (1,4,7-trioxanonanyl)-1-cyclohexanol (0.400 g, 0.797 mmol), and sodium hydride (0.0765 g, 2.0 equiv., 50%, unwashed) were added and the mixture was stirred for 4 hours. The reaction flask was immersed in a brine ice bath and cooled to −5° C. To the chilled solution, 3-nitrobenzyl bromide (0.362 g, 2.1 equiv.) dissolved in 25 ml of dry THF, was added over a 4 hour period. The reaction mixture was stirred at 0° C. for an additional 4 hours, then allowed to warm to room temperature. The mixture was then warmed and allowed to reflux for 24 hours. The solution was cooled, filtered through a Celite pad and the solvent removed in vacuo. The crude product was purified by column chromatography using 50/50 ethyl acetate/pet ether ($R_f$(prod)=0.41 on TLC) yielding pure 2-(2-napthoxy)-4,5-bis(1,4,7-trioxanonanyl)-cyclohexyl-3-nitrobenzyl ether, final product 8, as a yellow oil.

EXAMPLE 4

Figure 2:
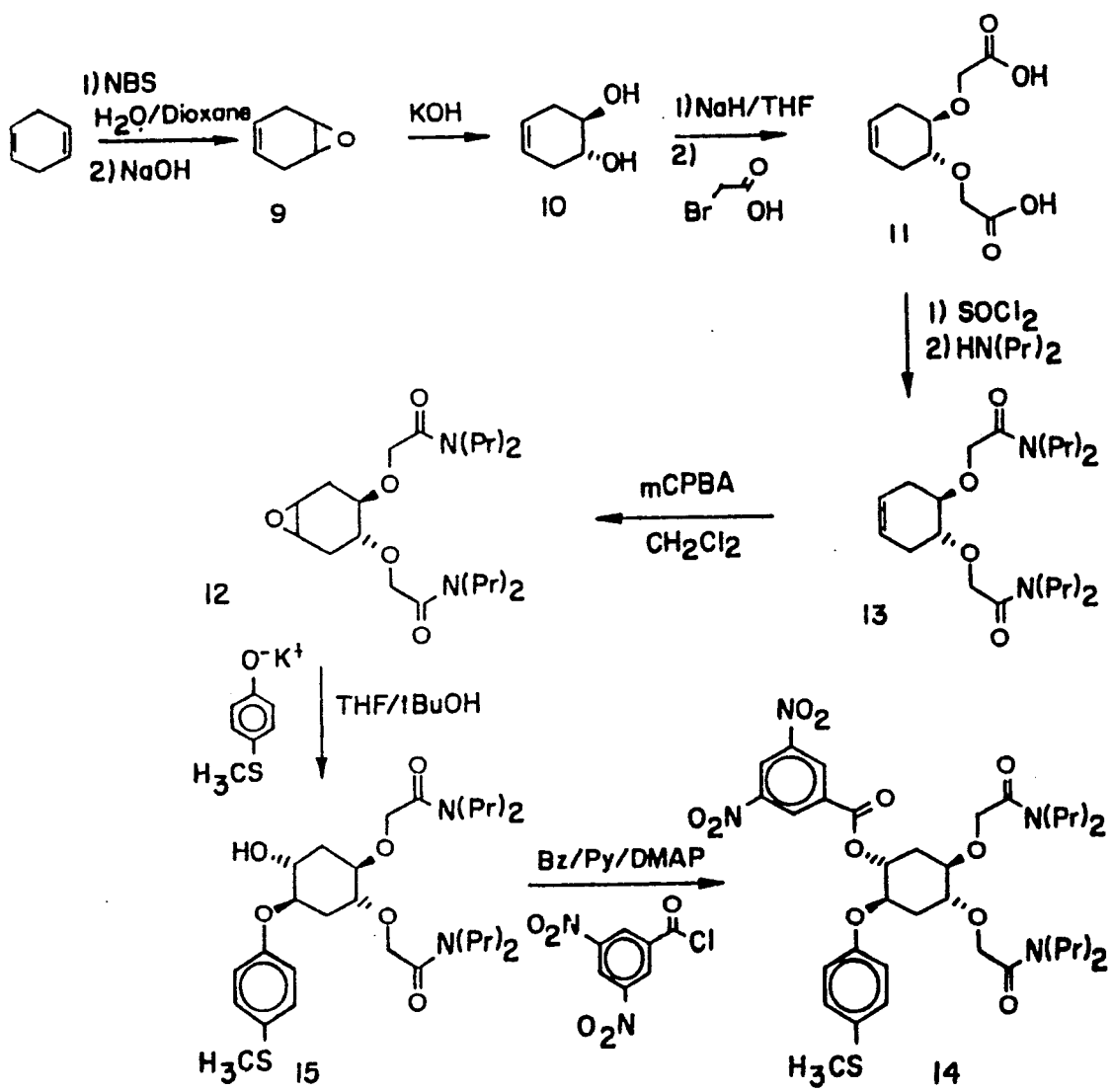

Synthesis of 1(R,S), 2(R,S), 4(R,S), 5(R,S)-4,5-bis-((dipropylcarbamoyl)-methoxy)-2-(4-methylthiophenoxy)-cyclohexyl-3,5-dinitrobenzoate The product was a result of the stepwise reaction scheme illustrated in FIG. 2. The reaction steps proceeded as follows.

A. 1,4-Cyclohexadiene (50.0 g, 0.626 mol) was added to a mixture of 225 ml of distilled water and 25 ml of p-dioxane. The mixture was stirred at 25° C. and N-bromo succinimide (108.9 g, 0.612 mol) was added slowly over a 1 hour period. The mixture was allowed to stir an additional 3 hours. The reaction mixture was then extracted 3 times with 100 ml portions of chloroform. The combined organic layers were then extracted 3 times with 50 ml portions of saturated aqueous sodium bicarbonate then dried over sodium sulfate and filtered. The solvent was removed in vacuo and the crude bromohydrin was immediately added to 1050 ml of a freshly prepared 1.0N sodium hydroxide solution and allowed to stir for 1 hour at 25° C. The reaction mixture was extracted three times with 100 ml portions of chloroform and the combined organic layers were dried over sodium sulfate and filtered. The solvent was removed in vacuo giving the crude epoxide which was distilled at 5 mm Hg. The fraction collected at 38°–40° C. (58.5 g, 97%) was shown to be [4.1.0] Bicyclo-7-oxo-hept-3-ene, subreaction product 9.

B. To 126 ml of a 6N solution of potassium hydroxide was added 15 ml of p-dioxane and 123.4 g (243.6 mmol) of [4.1.0] Bicyclo-7-oxo-hept-3-ene. The stirred mixture was allowed to reflux for 24 hours and then cooled to room temperature. 150 ml of brine was added and the mixture was extracted 7 times with 50 ml aliquots of chloroform. The combined organic layers were dried over sodium sulfate and the solvent was removed in vacuo. The resulting oil solidified upon standing giving the crude diol, which was dissolved in hot ethyl acetate, decolorized with activated charcoal and recrystallized from hot 75% ethyl acetate/25% heptane to give subreaction product 10; [1(R,S),2(R,S)] 4 Cyclohexen-1,2-diol, as white crystals, 15.9 g (57.4%): mp 97°–9° C.

C. A 500 ml flask was flame dried and fitted with a mechanical stirrer, condenser, and addition funnel. The flask was charged with 125 ml dry THF and [1(R,S),2(R,S)] 4 Cyclohexen-1,2-diol (4.0 g, 35 mmol) was added and stirred until all of the added solid had dissolved. To the solution, 18-crown-6 (0.200 g) and sodium hydride (6.90 g, 2.1 equivalents, 50% washed twice with hexane) were added and the mixture was stirred for 4 hours at room temperature. Bromoacetic acid (9.75 g, 2.0 equivalents, 85%) was dissolved in 100 ml of dry THF, transferred to the addition funnel and added dropwise to the reaction mixture over a 4 hour period. The dropping funnel was removed and the reaction flask was fitted with a heating mantle. The reaction mixture was warmed and allowed to reflux for 48 hours. The solvent was removed in vacuo and the residue was dissolved in 50 ml of saturated sodium bicarbonate. Concentrated hydrochloric acid was added to the solution until acidic to litmus (CAUTION: gas evolution) and the acidic aqueous solution was extracted 3 times with ether. The combined organic extracts were dried over magnesium sulfate and the solvent was removed in vacuo. The crude diacid was recrystallized from hot ethyl acetate yielding pure 1,(R,S),2(R,S)-1,2-bis(carboxymethoxy)-4-cyclohexane, subreaction product 11, as white crystals (27%). m.p. 87.5°–90° C.

D. A 50 ml flask was flame dried and fitted with a magnetic stirrer and drying tube. Dry benzene (10 ml), dry THF (10 ml) and 1,(R,S),2(R,S)-1,2-bis(carboxymethoxy)-4-cyclohexane (0.900 g, 3.91 mmol) were added to the flask and stirred until all of the added solid had dissolved. Thionyl chloride (1.384 g, 3.0 equiv.) was added and the mixture was stirred for 20 hours. The solvent was removed in vacuo and dry benzene (25 ml) was added. The process was repeated two more times, then a final addition of dry benzene (20 ml) was added and the reaction mixture was chilled to 0° C. in an ice bath. Dipropyl amine (2.764 g, 7.0 equiv.) was added and the solution was stirred for an additional 24 hours. The solvent was removed and the residue was dissolved in 50 ml of chloroform and extracted three times with 1N HCl, three times with saturated aqueous sodium bicarbonate and the layers separated. The organic layer was dried over magnesium sulfate, filtered and the solvent removed in vacuo leaving 1(R,S),2(R,S)-1,2-bis (dipropylcarbamoyl) methoxy-4-cyclohexene, subreaction product 12, (0.974 g, 63%) as a yellow oil.

E. A dry 100 ml flask was charged with methylene chloride (50 ml) and chilled in an ice bath to 0° C. 1(R,S),2(R,S)-1,2-bis(dipropylcarbamoyl) methoxy-4-cyclohexene (0.974 g, 2.53 mmol) and meta-chloroperoxy-benzoic acid (1.31 g, 3.0 equiv., 85% (tech)) were charged to the flask and stirred for 8 hours at 0° C. The reaction mixture was allowed to stand at room temperature overnight then the solvent was removed in vacuo with the bath temperature not exceeding 30° C. The residue was dissolved in diethyl ether (50 ml) and the solution was extracted three times with 20% aqueous sodium bisulfite, three times with saturated sodium bicarbonate and once with brine. The organic layer was dried over sodium sulfate, filtered and the solvent removed in vacuo. The epoxide was purified by column chromatography using 90/10 ethyl acetate/petroleum ether yielding the product of subreaction E as pure 1(R,S),2-(S,R),4(R,S),5(R,S)-4,5 bis((dipropylcarbamoyl)-methoxy-4-oxa-[4.1.0]-bicycloheptane (subreaction product 13) as a clear oil (0.48 g, 45%.

F. A 100 ml flask was flame dried, purged with dry nitrogen and fitted with a magnetic stirrer, heating mantle and condenser. Dry THF (25 ml), t-butanol (25 ml), potassium t-butoxide (0.700 g, 2.5 equiv.) and 4-methyl-thiophenol (1.0515 g, 3.0 equiv.) were added and the mixture was allowed to stir until all of the added solid had dissolved. 1,(R,S),2,(S,R),-4(R,S),4(R,S),5(R,S)-4,5-bis ((dipropylcarbamoylmethoxy)-4-oxa-[4.1.0]-bicycloheptane (1.030 g, 2.50 mmol) was added and the mixture was warmed and allowed to reflux for 72 hours. The reaction vessel was cooled to room temperature and the solvent was removed in vacuo. The residue was dissolved in diethyl ether and extracted 4 times with saturated sodium carbonate and once with brine. The organic layer was dried over sodium sulfate, filtered and the solvent was removed in vacuo. Pure product F was obtained by column chromatography of the residue with 100% ethyl acetate yielding pure 1,(R,S),2(R,S),4(R,S),5(R,S)-4,5-bis(dipropylcarbamoyl)-methoxy)-2-(4-methyl thiophenoxy)-cyclohexanol, subreaction product 14, (0.423 g, 31%) as a viscous oil.

G. A 50 ml flask was flame dried, fitted with a magnetic stirrer and a drying tube and charged with dry benzene (25 ml). Pyridine (0.242 g, 4.0 equiv.), dimethylaminopyridine (DMAP, 0.0050 g, cat) and 1,(R,S),2(R,S),4(R,S),5(R,S)-4,5-bis(dipropylcarbamoyl)-methoxy)-2-(4-methyl thiophenoxy)-cyclohexanol (0.423 g, 0.7663 mmol) were charged to the flask and allowed to stir until all of the added materials had dissolved. To the mixture, 3,5-dinitrobenzoyl chloride (0.530 g, 4.0 equiv.) was added and the solution was stirred for 72 hours. The solution was filtered and then extracted three times with 1N (HCl, three times with saturated sodium bicarbonate and once with brine. The solution was dried over sodium sulfate, filtered and the solvent removed in vacuo leaving final product 15, 1(R,S),2(R,S),-4R,S),5(R,S),4,5-bis((dipropylcarbamoyl)-methoxy)-2-(4-methylthiophenoxy-cyclohexyhexyl-3,5-dinitrobenozate as a yellow-orange oil which was further purified by column chromatography with ethyl acetate (0.545 g, 95%).

EXAMPLE 5

Complexation of $Na^{+1}$, $K^{+1}$, $Rb^{+1}$ and $Cs^{+1}$ by: 1(S,R), 2(S,R), 4(S,R, 5(S,R)-2-(4-methylthiophenoxy)-4,5-bis (1,4,7-trioxanonanyl)-cyclohexyl-3,5-dinitrobenzoate, 1(S,R), 2(S,R), 4(S,R), 5(S,R)-2-(2-napthoxy)-4,5-bis-(1,4,7-trioxanonanyl)-cyclohexyl-3,5-dinitrobenzoate, and 1(S,R), 4(S,R), 5(S,R)-2-(2-napthoxy)-4,5-bis (1,4,7-trioxanoanyl)-cyclohexyl-3nitrobenzyl ether A known amount of a charge transfer ionophore was dissolved in a solvent such as methanol and a premeasured amount of solid salt was added to the solution. Suitable salts include sodium nitrate, potassium bromate, potassium chloride and bromide, rubidium perchlorate and cesium chloride. The vial was shaken vigorously for about two minutes and the UV-visible absorption spectrum was taken. This was then subtracted from a spectrum of the free ionophore.

Figure 5:
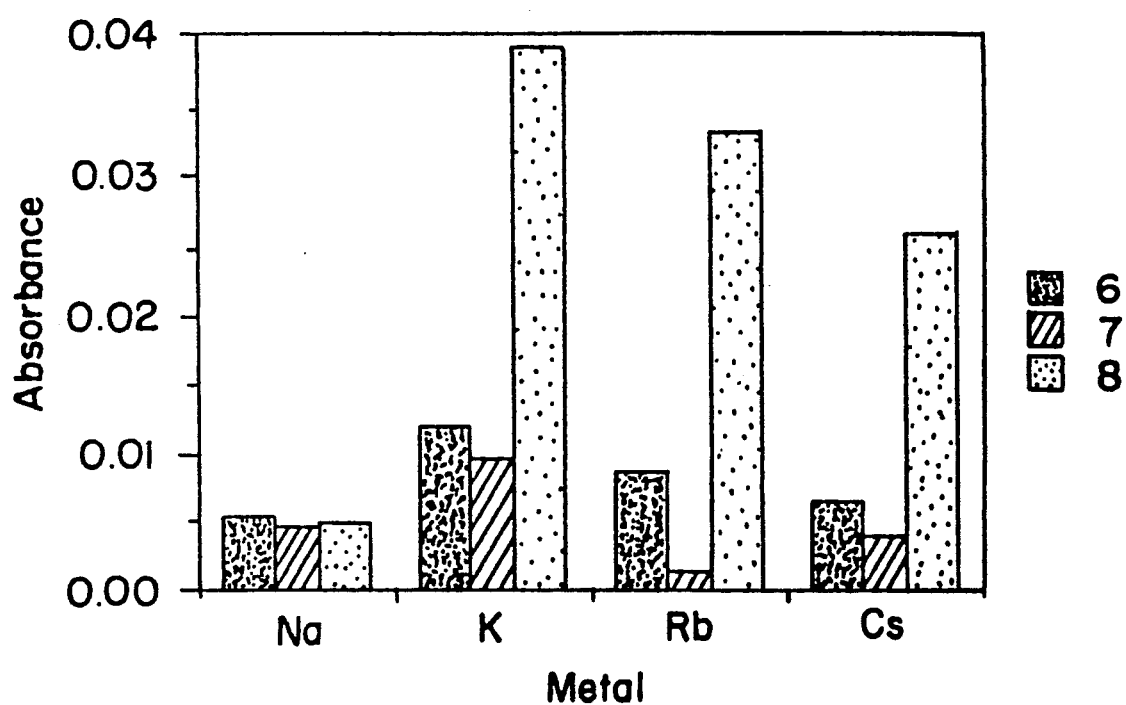

The effect of the addition of 1.0 equivalent of salt to 0.0050M solutions of the three ionophores: 1(S,R), 2(S,R), 4(S,R), 5(S,R)-2-(4-methylthiophenoxy)-4,5-bis (1,4,7-trioxanonanyl)-cyclohexyl-3,5-dinitro-benzoate, 1(S,R), 2(S,R), 4(S,R), 5(S,R)-2-(2-napthoxy)-4,5-bis (1,4,7trioxanonanyl)-cyclohexyl-3,5-dinitrobenzoate, and 1(S,R), 2(S,R), 4(S,R), 5(S,R)-2-(2-napthoxy)-4,5-bis (1,4,7-trioxanonanyl)-cyclohexyl-3nitrobenzyl ether, is plotted as FIG. 5.

EXAMPLE 6

Complexation of $Ca^{+2}$, $Mg^{+2}$ and $Sr^{+2}$ by: 1(S,R), 2(S,R), 5(S,R)-4,5-bis ((4-dipropylcarbamoyl)-methoxy)-b 2-(4-methylthiophenoxy)-cyclohexyl-3,5-dintrobenzoate A known amount of 1(S,R), 2(S,R), 5(S,R)-4,5-bis ((4-dipropylcarbamoyl)-methoxy)-2-(4-methylthiophenoxy)-cyclohexyl-3,5-dintrobenzoate was dissolved in a solvent such as methanol, acetonitrile, or nitromethane. A premeasured amount of solid salt was added to the solution. Suitable salts include magnesium nitrate hexahydrate, calcium nitrate tetrahydrate and strontium nitrate. The vial was shaken vigorously for about two minutes and the UV-visible absorption spectrum was taken. This was then subtracted from a spectrum of the free ionophore.

Figure 3:
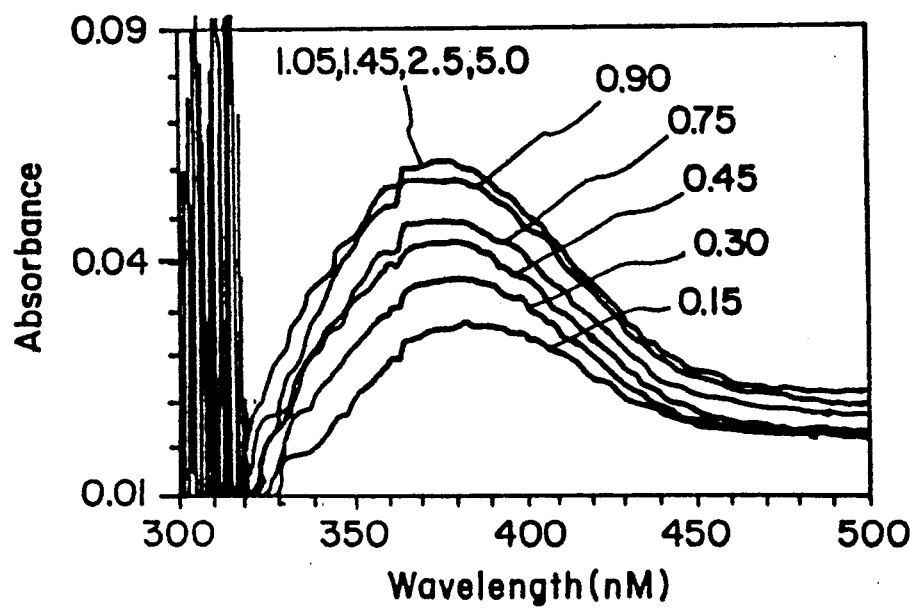
FIG. 3 is a chart of absorbance versus wavelength of products of the invention.
Figure 4:
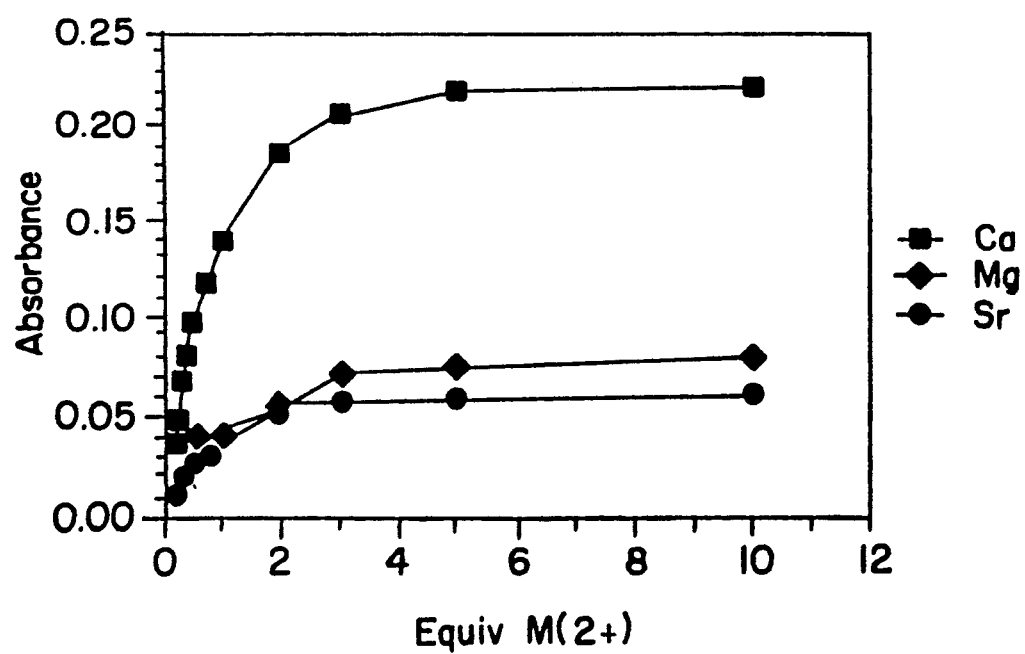
FIGS. 4 and 5 are charts of absorbance versus concentration of products of this invention.

The effect of salt addition to a 0.0050M solution of 1(S,R), 2(S,R), 5(S,R)-4,5-bis((4-dipropylcarbamoyl)-methoxy)-2-(4-methylthiophenoxy)-cyclohexyl-3,5-dintrobenzoate methanol is summarized on FIG. 3 and 4.

As can be appreciated from FIGS. 1 and 2 and the above examples, the preparation of desired electron acceptor and/or donor groups can be inserted as various reactants to make them present in the final product. The electron donor and acceptor reactants are preferably from 6 to 20 carbon atoms. Examples of suitable electron acceptor/donors are listed below with reference to a desirable reactant in FIGS. 1–2:

Electron Acceptors
  Acyl
    4-acetylbenzoyl chloride
    3-acylbenzoyl chloride
  Cyano
    3-cyano-benzyl chloride
    3-cyano-benzyl bromide
  Nitro
    4-nitrobenzyl chloride
    Nitrophenyl halides
    2-4-dinitro-1-chloro-benzene

| Desired Reactants For Above Electron Acceptors | Figure #, Product # |
| --- | --- |
| 2-(4-methylethiophenoxy-4,5-bis-(1,4,7-trioxanonanyl)-2-cyclohexanol | 1, 5 |
| 2-(2-napthoxy)-4,5-bis-(1,4,7-trioxanonanyl)-1-cyclohexanol | 1, 5 |
| 4,5-bis(dipropylcarbamoyl)-methoxy)-2-(4-methylthiophenoxy)-cyclohexanol | 2, 14 |

Electron Donors
  Amino Acid
    Tryptophan (11 carbons)
  Substituted Amines
    3-(n,n-dimethyl)-aminophenol
  Amidic Groups
    4-acetamidophenol
  Alkyl Thio
    4-methylthiophenol
  Hydroquinone
    resorcinol
  Mercaptophenol
    3-mercaptophenol

| Desired Reactants For Above Electron Donors | Figure #, Product # |
| --- | --- |
| 1(R,S), 2(S,R), 4(S,R) 5(S,R)-4,5-bis(1,4,7-trioxonanyl)-cyclohex-1-ene oxide | 1, 4 |
| 1(R,S), 2(S,R), 4(R,S), 5(R,S)-4,5-bis(dipropylcaramoyl)-methoxy)-4-oxa[4.1:0] bicycloheptane | 2, 13 |

It is contemplated that the invention can be utilized in the following manner to quantitatively determine the concentration of $Ca^{+2}$ in a sample of human or mammalian body fluid.

An organic extraction, using a suitable, non-$H_2O$ miscible organic solvent such as chloroform, methylene chloride, or ether containing a tetra substituted cyclohexane composition, will be performed on a sample of body fluid. After separation, the organic mixture will be subjected to a UV-spectrophotometer. Known amounts of $Ca^{+2}$ will be added to sample aliquots of the organic mixture. A plot of absorbance versus $[Ca^{+2}]$ will allow the determination of the $[Ca^{+2}]$ of the body fluid via interpolation or extrapolation.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

What is claimed is:

1. A method of detecting cations in a liquid comprising the steps of:
    a) providing a liquid containing metal or ammonium ions;

b) complexing the ion from the liquid by treating the liquid with an effective complexing amount of a tetra substituted cyclohexane composition;

wherein the tetra substituted cyclohexane has an ionophore in the 1,2 positions wherein the ionophore may be the same or different and is selected from the group consisting of a crown, a podand and a cryptand; and wherein positions 4,5 are substituted by an electron donor group and an electron acceptor group.

2. The method of claim 1 wherein the cyclohexane is in the chair form.

3. The method of claim 2 wherein the ionophore of the chair form is the diequatorial isomer.

4. The method of claim 2 wherein the ionophore is the diaxial position.

5. The method of claim 2 wherein the tetra substituted cyclohexane has the following structure:

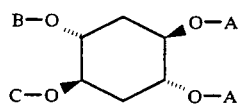

wherein A is the ionophore and B and C is the electron donor or the electron acceptor groups.

6. The method of claim 2 wherein the electron acceptor group is a nitro substituted benzoyl.

7. The method of claim 2 wherein the electron donor is an araloxy group of from six to twenty carbon atoms.

8. The method of claim 2 wherein the electron donor is a thioaryl group of from six to twenty carbon atoms.

9. The method of claim 2 wherein the tetra substituted cyclohexane has the following structure:

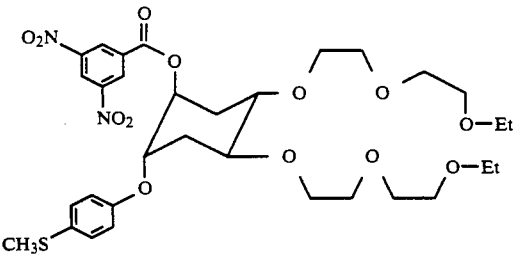

10. The method of claim 2 wherein the tetra substituted cyclohexane has the following structure:

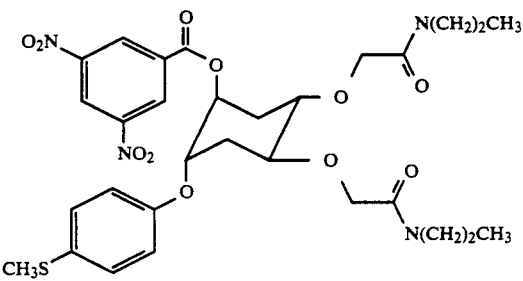

11. The method of claim 2 wherein the liquid is a liquid from a mammal.

12. The method of claim 2 wherein the cation is an alkali metal ion.

13. The method of claim 2 wherein the cation is an alkaline earth metal cation.

14. The method of claim 11 wherein the ionophore is a crown.

15. The method of claim 1 wherein the ionophore is a podand.

16. The method of claim 1 wherein the ionophore is a cryptand.

* * * * *